United States Patent [19]

Kackos

[11] 4,325,906
[45] Apr. 20, 1982

[54] PROCESS FOR QUIETING STEAM INJECTED INTO WATER IN A STERILIZER

[75] Inventor: Edward M. Kackos, Belmar, N.J.

[73] Assignee: Vernitron Corporation, Lake Success, N.Y.

[21] Appl. No.: 196,206

[22] Filed: Oct. 14, 1980

[51] Int. Cl.³ ............................ A61L 2/06; A61L 2/20
[52] U.S. Cl. ........................................ 422/26; 422/34; 422/38; 422/295
[58] Field of Search .................. 422/25, 26, 27, 38, 422/34, 295, 292, 302, 307, 1

[56] References Cited

U.S. PATENT DOCUMENTS 3,093,449  6/1963  Kotarski et al. ................. 422/25 X
3,954,406  5/1976  Chamberlain ..................... 422/27

Primary Examiner—Barry Richman
Attorney, Agent, or Firm—Edward H. Loveman

[57] ABSTRACT

Apparatus and a process for quietly injecting live, high pressure steam into water in a sterilizer chamber, wherein a minute quantity of air at higher pressure than the steam is quietly mixed with the steam prior to passing the stream of air mixed with steam into water in the chamber. The water can be drawn from the chamber by a recirculating pipe into a venturi ejector into which the stream of air mixed with steam is passed. The water quietly mixes with the stream of air and steam and the combined stream of air, steam and water is quietly recirculated back into the chamber.

2 Claims, 1 Drawing Figure

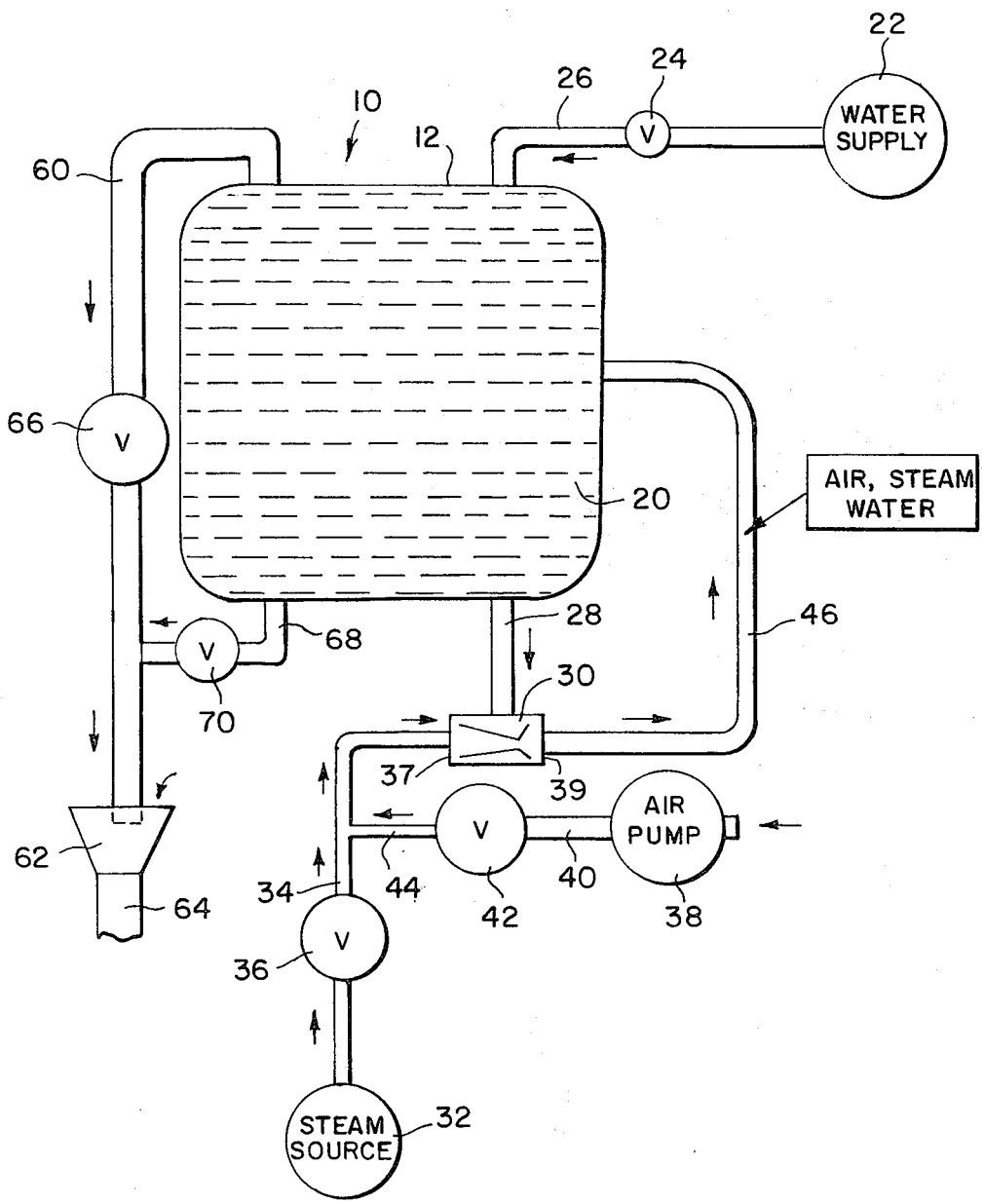

PROCESS FOR QUIETING STEAM INJECTED INTO WATER IN A STERILIZER

This invention relates to the art of sterilizers used for steam sterilization of surgical instruments and other articles; and more particularly concerns an apparatus and process to quiet the steam when injected into relatively cold water in a sterilizer.

Heretofore, it has been conventional to preheat a sterilization chamber by filling a sterilization chamber with cool water and then injecting live steam into the body of cool water. When the live steam is injected into water, it is accompanied by loud hissing and banging as the steam condenses in the water and as millions of bubbles are generated and break. This is a highly objectionable condition in or near an operating room where such a sterilizer is often used.

The only solution proposed heretofore has been to locate the sterilizer in a room adjacent the operating room, where, hopefully, the noise will not be heard, or will be held at tolerable levels.

The present invention employs a novel approach to the noise problem encountered with conventional steam sterilizers. According to the invention, air is injected into, and mixed with the stream of steam before it is injected into the relatively cool or cold water in the sterilization chamber and/or the jacket chamber surrounding the sterilization chamber. For steam having a pressure about 35 pounds per square inch, air is injected at 45 pounds per square inch. Then the mixture of air and steam is injected into the cool or cold water. The steam and air stream enters the body of water and condenses quietly. Also, bubbles are generated quietly in the water, and break quietly, i.e., at very attenuated tolerable levels as compared with the loud hissing and banging heretofore encountered. It has been discovered that the rate of steam collapse, as it contacts the cold water, is slowed sufficiently so that the steam condenses quietly while warming the body of water. The quantity of air in the steam is regulated so only a very small quantity of air is present in the steam, just sufficient to have the desired quieting effect. The bubbles of steam are mixed with bubbles of air, so that both generation and collapse of the bubbles in water are almost silent.

It is, therefore, a principal object of the present invention to provide apparatus which will enable mixing of a minute quantity of air under high pressure with live steam under pressure, less than the air pressure, prior to injecting the stream of air and steam into a body of water in a sterilization chamber and/or a jacket chamber surrounding the sterilization chamber.

A further object of the present invention is to provide a process for quieting steam entering a body of water in a sterilizer by injecting air into the steam before it is injected into the water.

These and other objects of this invention will be readily perceived from the following detailed description of the invention, when read in connection with the appended drawing.

The single FIGURE of the drawing is a schematic diagram of a steam sterilizer adapted by and embodying the invention for quieting the flow of steam entering a body of water in the sterilizer.

Referring now to the drawing, there is illustrated a steam sterilizer, generally designated as reference numeral 10, having walls 12 defining an inner closed sterilization chamber 16, which is filled with water 20. The wash water 20 is supplied from a source of supply 22, a pipe 26, and a valve 24.

Overflow of the water 20 out of the chamber 16, is through an overflow drain pipe 60, opening into the top of the chamber 16. The pipe 60 empties into a funnel 62, of a drain 64. The top of the drain funnel 62 is open to atmosphere. A drain valve 66 is set to control flow of water through the pipe 60. This valve may have a steam trap to prevent passage of steam through the pipe 60. Water is drained out of the bottom of the chamber 16 via a drain pipe 68, controlled by a valve 70, and connected to the drain pipe 60.

The water 20 is heated by recirculation. The water 20 is drawn out of a pipe 28 which opens into a side of a venturi steam ejector 30. Live steam at about 35 pounds per square inch is supplied from a steam source 32, and passes up a steam feeder pipe 34 via regulator valve 36 to one end 37 of the venturi ejector 30. An air pump 38 is connected via a pipe 40, to a regulator valve 42 to supply air at about 45 pounds per square inch. The valve 42 can be throttled so that only a minute quantity of air passes through the valve 42 to an air feeder pipe 44, connected to a side of the pipe 34. The mixture of air and steam enters a venturi inlet 37, where it mixes with the water 20. The mixture of air, water, and steam, leaves outlet 39 of the venturi ejector and passes via a recirculator pipe 46 back to the chamber 16. The mixing of air and steam in the pipe 34, the mixing of the stream of air and steam with water in the venturi ejector 30 and the passage of the mixture of air, steam, and water into the chamber 16 are all relatively quiet, and almost silent as compared with the prior hissing and banging heretofore encountered when injecting steam into a water filled jacket of a steam sterilizer.

To the extent described, the invention applies to both a washer type of sterilizer described above, and to an ethylene oxide type of sterilizer, which employs a water jacket surrounding the sterilization chamber for heating the sterilization chamber. While the process has been described using a recirculation system, it is contemplated that the air-steam mixture could be injected directly into the body of water in the sterilization chamber or jacket therefor.

It should be understood that the foregoing relates to only a limited number of preferred embodiments of the invention which have been by way of example only and that they are intended to cover all changes and modifications of the examples of the invention, herein chosen for the purpose of the disclosure, which do not constitute departures from the spirit and scope of the invention.

What is claimed is:

1. A process for quietly injecting steam having air inherently present therein into a body of water in a sterilizer chamber, comprising the steps of:
   supplying steam at high pressure;
   continuously mixing minute quantities of air quietly with said steam, said air being at a higher pressure than said steam pressure; and
   continuously injecting quietly a stream of said air, mixed with said steam into said body of water.

2. A process for quietly injecting steam having air inherently present therein into a body of water in a sterilizer chamber, comprising the steps of:
   supplying steam at high pressure;
   continuously mixing minute quantities of air quietly with said steam, said air being at a higher pressure than said steam pressure;
   removing water from said chamber;
   continuously injecting quietly said stream of air, mixed with said steam, into said water removed from said chamber; and
   recirculating quietly said water mixed with said stream of air and steam into said chamber.

* * * * *